(12) United States Patent
Abbasi

(10) Patent No.: US 6,786,863 B2
(45) Date of Patent: Sep. 7, 2004

(54) METHOD AND APPARATUS FOR REMOTE PHYSICAL CONTACT

(75) Inventor: Touraj Abbasi, Baku (AZ)

(73) Assignee: DADT Holdings, LLC, Westlake Village, CA (US)

(*) Notice: Subject to any disclaimer, the term of this patent is extended or adjusted under 35 U.S.C. 154(b) by 0 days.

(21) Appl. No.: 09/906,949

(22) Filed: Jul. 12, 2001

(65) Prior Publication Data

US 2002/0188186 A1 Dec. 12, 2002

Related U.S. Application Data

(60) Provisional application No. 60/296,907, filed on Jun. 7, 2001.

(51) Int. Cl.$^7$ .................................................. A61F 5/00
(52) U.S. Cl. ......................................... 600/38; 709/200
(58) Field of Search ................................. 345/753, 702, 345/161; 370/260; 709/204, 236; 600/38, 39, 300; 340/407.1; 361/1; 700/85; 463/38

(56) References Cited

U.S. PATENT DOCUMENTS 5,375,068 A * 12/1994 Palmer et al. ............... 345/753
6,368,268 B1 * 4/2002 Sandvick et al. ............ 600/38

2002/0191011 A1 * 12/2002 Rasouli ...................... 345/702

FOREIGN PATENT DOCUMENTS

DE        WO 8806077 A2 *  2/1988 ............. B25J/3/04

OTHER PUBLICATIONS

White, Ron, How Computers Work, Sixth Edition, pp. 282–283.*
Brave et al, Tangible Interfaces for Remote Collaboration and Communication, 1998, Proceedings of CSCW 1998, pp. 1–10.*
Tele Immersion, Oct. 21, 2000, pp. 1–5.*
FuckU–FuckMe, http://www.fufme.com, Mar. 8, 2000, p. 1–5.*

* cited by examiner

*Primary Examiner*—Eric F. Winakur
*Assistant Examiner*—Brian Szmal (57) ABSTRACT

Remote physical contact using mechanical surrogates that replicate anatomical components. Pressure, temperature and displacement sensors perceive action upon the surrogate. Actuators for pressure temperatures and displacement enable a second surrogate to mimic the contact imparted on the first. A computer program implements the method by sending contact messages comprising contact characteristics that describe the nature of a physical contact perceived by a surrogate with full duplex capability. A human lip surrogate enables two people to kiss remotely.

14 Claims, 6 Drawing Sheets

METHOD AND APPARATUS FOR REMOTE PHYSICAL CONTACT

RELATED APPLICATIONS

This application is a utility application that claims priority to a provisional parent application, application No. 60/296,907, filed with the Office on Jun. 7, 2001.

BACKGROUND OF THE INVENTION

1. Technical Field

This invention pertains to the field of remote physical interaction.

2. Description of the Prior Art

Human contact has always involved stimulation of other people's senses, be it at an informal level or in a more intimate context. The need for sensory perception during the course of human contact can be driven by a myriad of motives. In one context, human emotional involvement has always led to an affectionate caress of a potential or current mate.

Men and women hold hands, kiss and engaged in more prurient appealing activities. In another context, physicians are required to touch their patients in order to facilitate a diagnosis. These two forums of human contact have vary disparate motivation, but the need to make a physical contact with another human being is no less compelling in any venue. Physical contact has always been a means for enhancing communications.

With the advent of modern telecommunications, doctors can now see their patients remotely. Video teleconferencing has helped specialized medical practitioners visit patients that could not otherwise be attended to. Video teleconferencing has also enabled a whole new generation of people to meet and socialize without ever having to leave their homes.

In this age of networked computers, the ability for people to communicate over vast distances is uncontroverted. The form of this communication, though, continues to comprise textual messaging, audio and video information.

The traditional use of sight and sound for communication over a computer network brings many people together. Doctors can perform virtual house calls and people can meet each other for social or business purposes.

As effective as audio and video is for communication, it does not provide for the tactile sensation so inherent in many forms of human contact. Once people meet over a computer network, they are apt to desire some form of physical contact. The prior art has not provided a means for these people to shake hands, share a kiss or to engage in other, more private forms of physical contact. Likewise, physicians have no means available to remotely touch a patient.

A doctor affecting a diagnosis may in fact need to explore the body of the patient in order to procure an effective diagnosis. Video based examination of a patient is fairly effective, but the tactile response a doctor perceives by touching the patient can be an invaluable method of determining the cause of a physical condition.

What is lacking in the known art is a means of transmitting tactile or other physical stimulus from one human user to another. The present invention does just this, it enables people to expand on the notion of teleconferencing or computer communications by adding a capability to engage in all types of physical contact.

SUMMARY OF THE INVENTION

The present invention comprises a method and apparatus that enable remote physical contact. The method of the present invention comprises the steps of using a first mechanical surrogate attached to a first computing device. The mechanical surrogate can me any anatomical component. The first mechanical surrogate further comprises sensors that enable the mechanical surrogate to detect actions imparted onto it. Such actions could comprise temperature, pressure or physical displacement. These actions are perceived by the appropriate sensors for temperature, pressure or displacement. The types of actions perceived and the types of sensors disposed in the mechanical surrogate can vary with the application and hence any or all of these types of sensors can be used collectively or in any possible combination.

A user specifies the address of a remote computing device as either a logical or physical address. Using this address, the first computing device will establish a connection with a second computing device that has a second mechanical surrogate attached thereto. The second mechanical surrogate comprises actuators that enable it to mimic the actions imparted onto the first mechanical surrogate. The first computing device monitors the sensors disposed in the first mechanical surrogate and creates contact messages that reflect the state of the first surrogate. The contact message can be though of as carrying information indicative of the action imparted on the first mechanical surrogate.

The first computing device then conveys the contact message to the second computing device where it is processed and used to command actuators disposed in the second mechanical surrogate. The actuators in the second surrogate comprise any combination of thermal (heater and cooler), pressure and displacement actuators. In many applications the first and second surrogates are counterparts of each other. This most commonly pertains to a hand that is used as the second surrogate and a glove that is used as a first surrogate.

In order to provide for a full-duplex capability, the method of the present invention further teaches the step of receiving sensory input from the second surrogate in the second computing device. This allows the actions imparted onto the second surrogate to be perceived by sensors disposed thereon or therein. Because each surrogate is actively manipulated in response to contact messages received from the opposing computer, there exists the possibility for positive feedback.

The method of the present invention teaches that the feedback from the second surrogate be attenuated by action components induced by commanding of the actuator.

Once the feedback is attenuated, the second computing device creates a contact message that reflects the attenuated, or buffered sensory signals. These contact messages are conveyed to the first computing device so that the first surrogate can be commanded to mimic the actions imparted onto the second surrogate.

The method of the present invention further defines a step for receiving video information from a video camera attached to the first computing device and then conveying the video in a compressed format to the second computing device.

Once the compressed video arrives at the second computing device, it is presented on a graphic display. This provides a visual perception of the contact episode embodied in the manipulation of the mechanical surrogates.

The method of the present invention also claims the capability to receive audio information from a microphone attached to the first computing device. The audio is then conveyed to the second computing device where it is routed to a speaker system or audio output unit.

The method of the present invention further defines a capability for receiving text from a keyboard attached to the first computing device, conveying the text to the second computing device and then displaying the text on a graphic display on the second computing device.

All conveyance from the first computing device to the second computing device of audio, video and/or textual data is accomplished by way of the communications link.

The method of the present invention is embodied in a computer program. The computer program comprises an interface manager, a sensor process and a response actuator process. The sensor process receives sensor inputs from a mechanical surrogate and creates contact messages indicative of the actions imparted onto the surrogate. The sensor processor then conveys the contact message to a remote process by way of computer readable media.

The response actuator process receives a second contact message from a remote process also by way of computer readable media. The response actuator process then commands actuators in or on a mechanical surrogate in order to conform the surrogate to a contact as defined in the second contact message.

Although the most common form of computer readable media that is used to convey contact messages would be a network, as for instance the Internet, rotating media can also be used. Rotating media may be an effective means of storing contact characteristics for future replication.

The contact messages sent and received by the computer program comprise various contact characteristic fields. Some of these include a temperature characteristic field, a pressure characteristic field and a displacement characteristic field.

The computer program further comprises a graphical user interface manager that presents a graphical user interface comprising an address acceptance window, and command buttons to start and stop a contact encounter. The graphical user interface manager sends the address, which can be either logical or physical, to the interface manager. The interface manager uses the address to establish a communication link with a corresponding process.

The graphical user interface manager further presents a textual chat window. The graphical user interface manager conveys the text that is acquires from a keyboard to the interface manager. The graphical user interface manager also receives text from the interface manager and presents it in the textual chat window. The graphical user interface manager can also present a video display window and display video data that it receives from the interface manager.

The invention also comprises a mechanical surrogate in the form of a human lip. The human lip surrogate comprises upper and lower lips formed from a pliable material and lip actuators and sensors. The lips can be formed from silicon. The lip actuators can be any combination of heater-coolers, pressure actuators or displacement sensors. The sensors disposed on or in the lip can be thermal sensors, pressure sensors or displacement sensors. Any combination of these can be used. The human lip surrogate further comprises a mounting flange to facilitate mounting of the surrogate.

BRIEF DESCRIPTION OF THE DRAWINGS

The foregoing aspects are better understood from the following detailed description of one embodiment of the invention with reference to the drawings, in which.

DETAILED DESCRIPTION OF THE INVENTION

Figure 1:
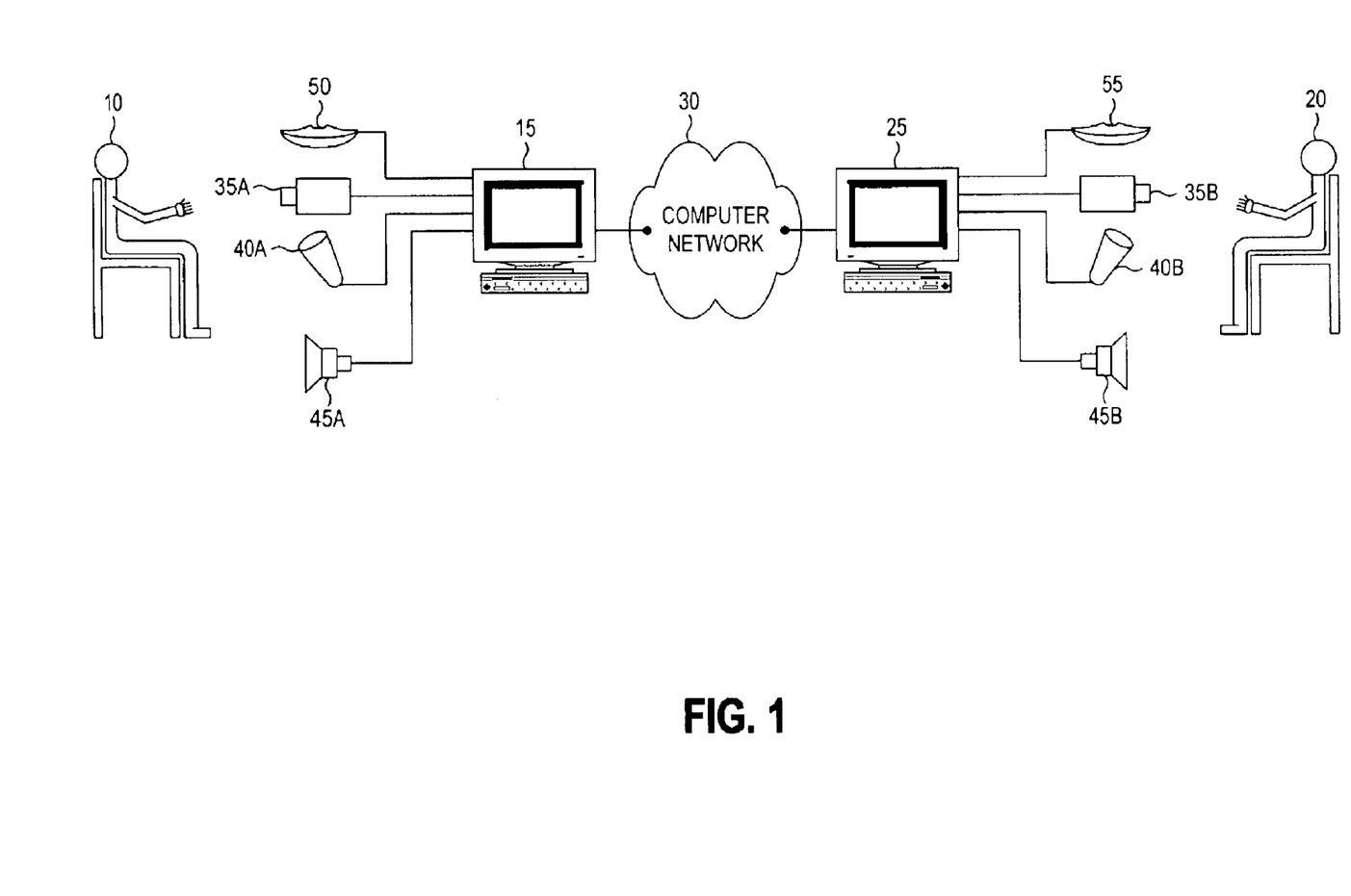
FIG. 1 is a block diagram that depicts a human physical contact system according to the present invention.

FIG. 1 is a block diagram that depicts a human physical contact system according to the present invention. A first computer user 10 interacts with a second computer user 20 in order to affect a physical contact between the two. Both computer users utilize a computer, or some other computing device comprising a processor capable of executing a sequence of instructions. The first computer user uses a first computer 15 while the second computer user uses a second computer 25. The first computer 15 and the second computer 25 communicate over a computer network 30 or other computer readable media. In many operational scenarios, the computer network will be the Internet. In some operational scenarios, the two computers need not communicate in real time. This means that the computer readable media need not be a network, but can be a rotating media such as floppy diskette, hard disk, CD-ROM or DVD.

Each computer interfaces to a plurality of external sensory devices including, but not limited to a video camera (35A and 35B), a microphone (40A and 40B), and a speaker (45A and 45B). These sensory devices can be used optionally, collectively or in any combination.

Further comprising the system are mechanical surrogates 50 and 55. The mechanical surrogates can comprise replicas of human anatomical components. The mechanical surrogates further comprise sensors and actuators needed to mimic natural human contact.

Figure 2:
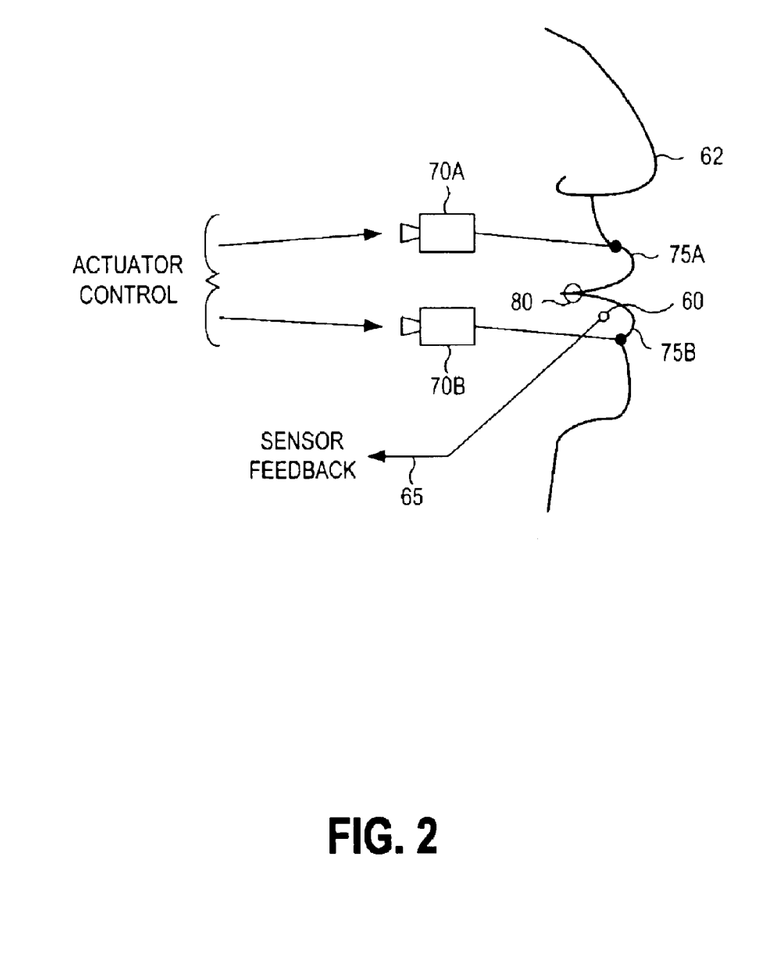
FIG. 2 is a pictorial of a human lip surrogate according to the present invention. In a human lip, sensors 60 are disposed around the periphery of the lip.

FIG. 2 is a pictorial of a human lip surrogate according to the present invention. In a human lip, sensors 60 are disposed around the periphery of the lip. Such sensors can further comprise pressure sensors, temperature sensors and displacement sensors. The feedback from the sensors 65 is routed back to the computers (15 or 25) for processing in accordance with further description presented infra.

Control actuators 70 are driven by the computers so that sensory perceptions registered by the first computer 15 are reflected on the human lip surrogate attached to the second computer 25. Control actuators 70 can comprise pressure applicators, thermal controls (heater-coolers), or displacement actuators such as linear motors or pulley driven actuators.

In practice, a user can kiss the mechanical surrogate attached to the first computer 15. The user's kiss can be perceived through the sensors located in the first mechanical surrogate 50. The characteristics of the kiss, as defined by the sensor feedback, can be communicated by the first computer 15 to the second computer 25 using a computer network 30. Once the characteristics of the kiss are received, the kiss can be recreated on the second mechanical surrogate 55 attached to the second computer 25. To complete the contact sequence, the second user 20 can kiss the mechanical surrogate 55 attached to the second computer 25. The mechanical surrogates 50, 55 continuously exchange stimulus and response by accepting sensor input at one surrogate and replicating the characteristics of the kiss at the other surrogate. This process happens in real or near real time.

In one preferred embodiment, a human lip surrogate 62 is comprised of a human lip model molded from a pliable material such as silicon, but silicon is not an exclusive formulation for any surrogate component. In this preferred embodiment, the silicon lip model is molded to present a closed mouth with a partial cavity 80 behind the lips 75. As the control actuators 70 are engaged, the upper lip 75A or the lower lip 75B are pulled open. This can be accomplished in unison or on an independent basis. The control actuators 70 can be made linear so that subtle lip gestures can be recreated. In one refinement of the present invention, teeth can be disposed in the mouth cavity 80 thereby adding more realism to a kissing experience. Facial hair can be applied to the mechanical surrogate to further enhance the contact episode. The human lip surrogate can further comprise a mounting flange to enable attachment to a computer or to another surface.

Figure 3:
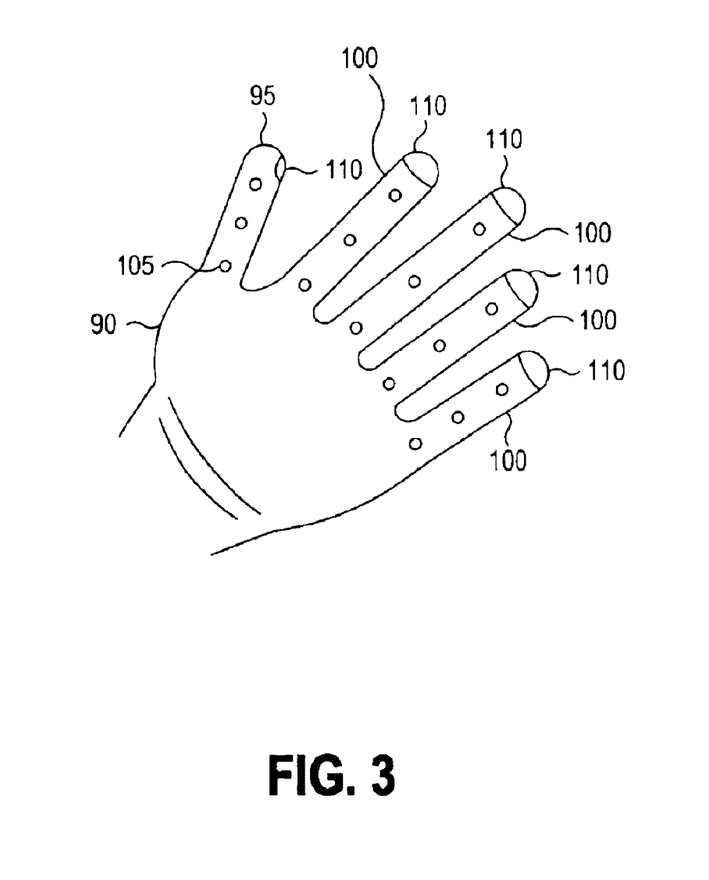
FIG. 3 is a pictorial representation of a human hand interface.

FIG. 3 is a pictorial representation of a human hand interface. One significant advent of the present invention is the notion of having complimentary surrogate apparatus. In the case of patient diagnosis, a doctor would use a human hand interface 90. The human hand interface 90 is worn on the hand analogous to a glove. In one preferred embodiment, the human hand interface 90 comprises a thumb sleeve 95 and four finger sleeves. Each sleeve further comprises a plurality of displacement sensors 105. The displacement sensors detect movement of the user's fingers in the glove. Each sleeve further comprises tactile actuators. These tactile actuators apply surface pressure to the fingers in the glove.

Figure 4:
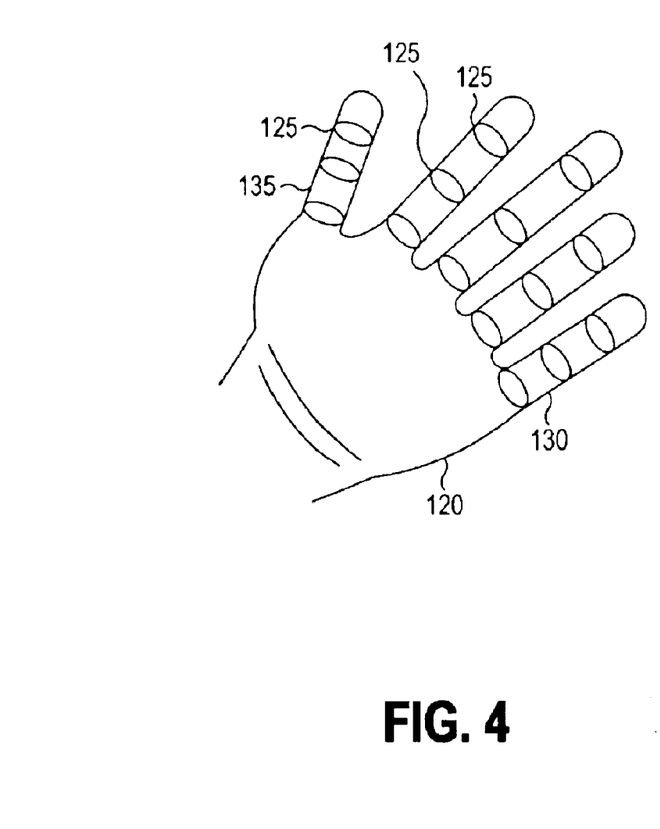
FIG. 4 is a pictorial representation of a human hand surrogate.

FIG. 4 is a pictorial representation of a human hand surrogate. The human hand surrogate 120 is the complimentary surrogate to the human hand interface 90. Where the human hand interface 90 has displacement sensors, the human hand surrogate comprises linear displacement actuators 125 that manipulate the fingers 130 or thumb 135.

Figure 5:
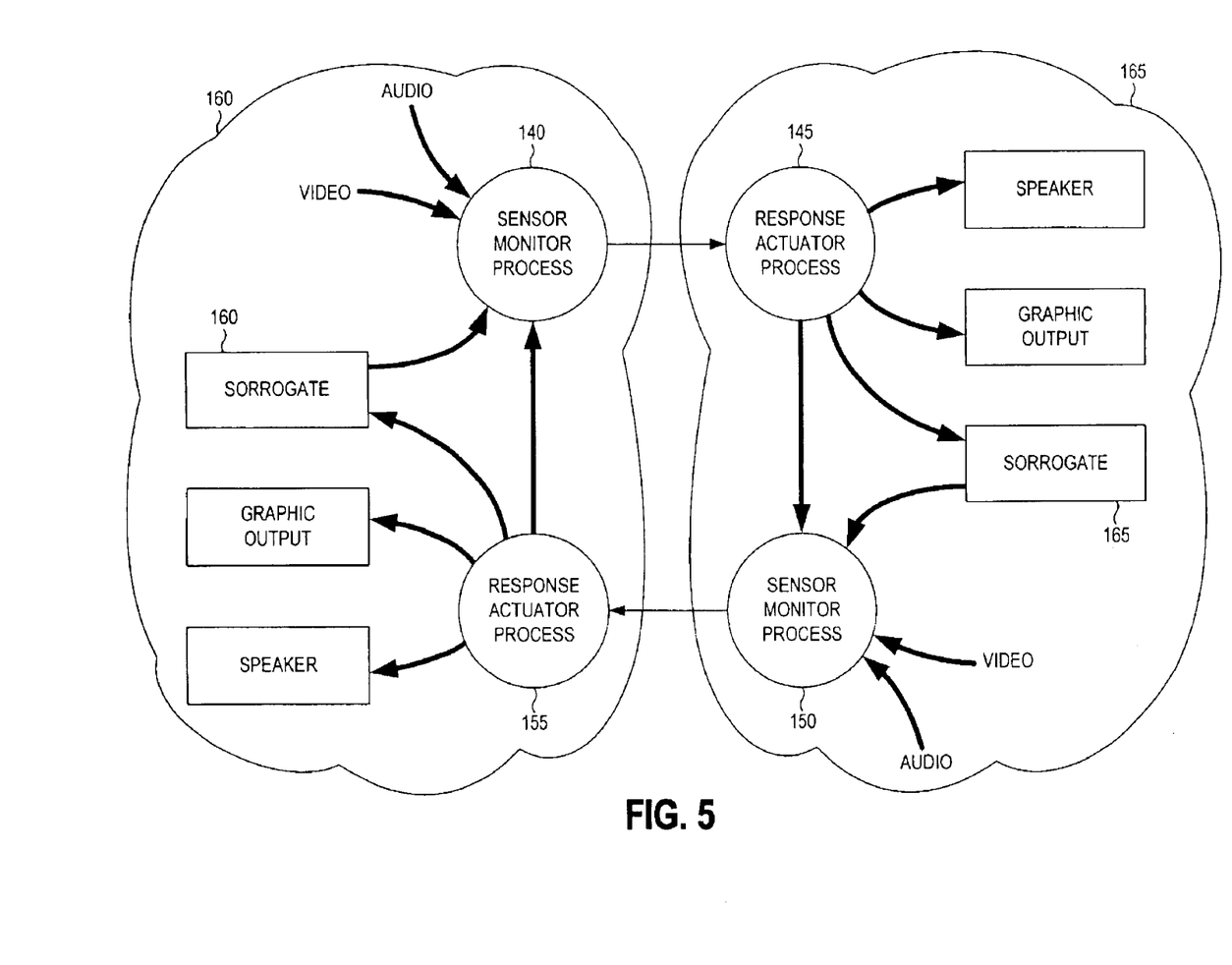
FIG. 5 is a data flow diagram that depicts the transfer of surrogate actions from a first computer to a second computer.

FIG. 5 is a data flow diagram that depicts the transfer of surrogate actions from a first computer 15 to a second computer 25. Complimentary processes are launched on each of said first and second computers (15 and 25). These processes are a sensor monitor 140 and a response actuator 145.

A second set of complimentary processes is launched in the first and second computers (15 and 25). These are identical, but transposed processes. This means that there is a first sensor process 140 executing in the first computer 15 and a second sensor process 150 executing in the second computer 25. Likewise, a first response actuator process 145 executes in the second computer 25 while a second response actuator executes in the first computer 15. A task scheduler ensures that all processes execute in timely and essentially simultaneous fashion.

The first sensor monitor process 140 accepts inputs from sensory devices comprising video, audio and mechanical surrogates 160. For the purposes of the present invention, the audio and video input devices are optional. The first sensor monitoring process 140 accepts input from sensors mounted in or on a first mechanical surrogate 160. These sensory signals are formatted into a contact characteristics message (CCM) and conveyed to the first response actuator process 145.

The first response actuator process 145 receives a CCM from the first sensor monitoring process 140, decodes the message and conveys commands to the second mechanical surrogate 165. The second mechanical surrogate 165, in turn, is manipulated in order to replicate the actions experienced by the first mechanical surrogate 160.

The CCM is a general purpose response message that conveys the pressure, temperature and displacement imparted on the first mechanical surrogate and perceived by the appropriate sensors disposed on or therein. Optional video and audio information are conveyed to the first response actuator process 145 using known formats for compressed audio and video transmission.

As the second mechanical surrogate 165 is activated by the first response actuator process 145, it will stimulate the sensors that are used to perceive actions imparted onto it by a second user. In the case of a human lip surrogate, motion caused by activation of the control actuators 70 will cause the displacement and pressure sensors to perceive external stimulus. To prevent this type of unwanted feedback, the first response actuator process 145 conveys the actuator commands to the second sensor monitor process 150. These actuator commands allow the second sensor monitor process 150 to eliminate those components from the sensory feedback provided by the second mechanical surrogate 165.

The contact experience is brought full circle by allowing the sensor array inputs received from the second mechanical surrogate 165 to be conveyed by the second sensor monitoring process 150 to the second response actuator process 155.

The processes depicted in FIG. 5 are embodied in a computer program. A first instance 160 of the program executes in the first computer 15 while a second instance 165 of the program executes in the second computer 25. It should be noted that any process could be used to replace either of these program instances so long as the functional interface compatibility between any remaining instance of the program and the replacing process is achieved.

Figure 6:
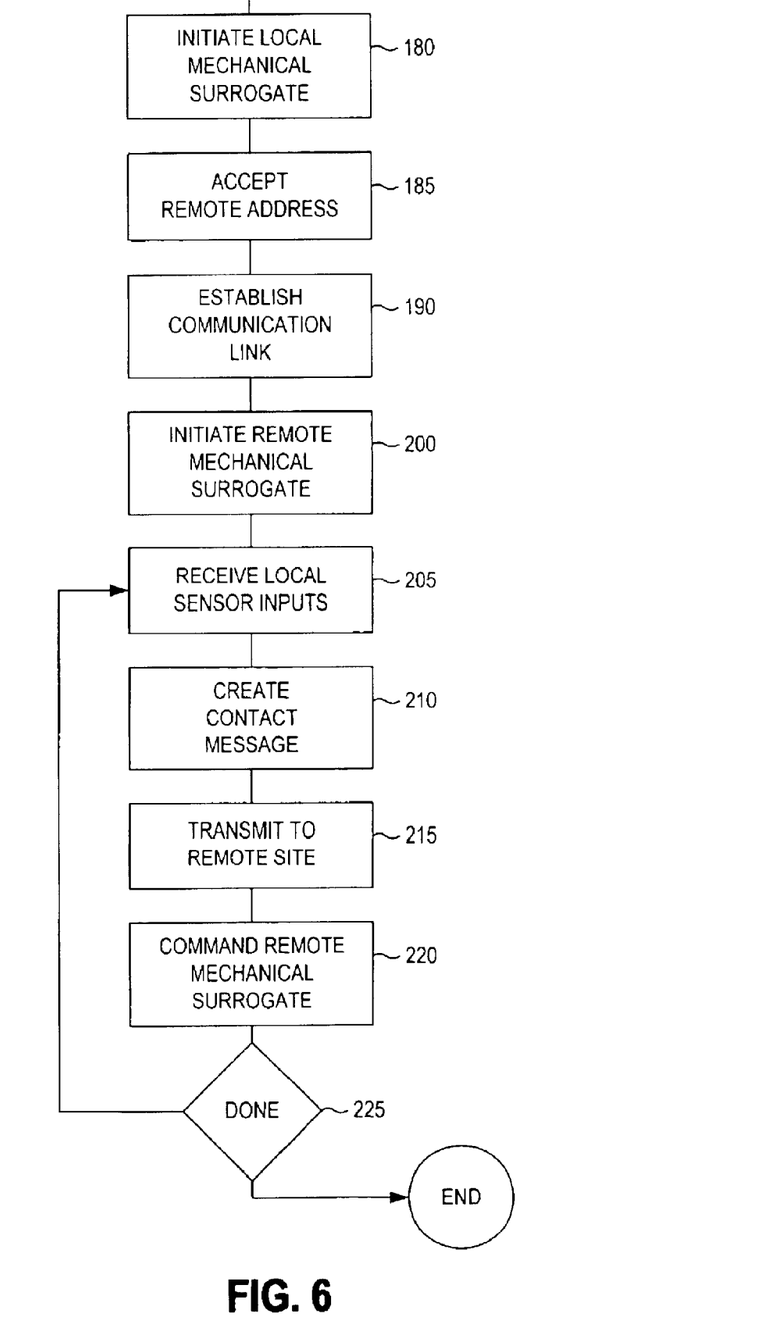
FIG. 6 is a process flow diagram that summarizes the method of affecting remote physical contact according to the present invention.

FIG. 6 is a process flow diagram that summarizes the method of affecting remote physical contact according to the present invention. In the first step (step 180), a local mechanical surrogate is initiated. Once that surrogate is initiated, the computer program accepts a destination address (step 185) so that a peer-to-peer connection can be established (step 190). The address received by the computer program can be either a logical address or a physical address. In some embodiments, a physical address is preferable to ensure security in a contact encounter.

Once the remote computer is contacted, a remote surrogate is initiated (step 200). The computer program begins a loop in which it receives sensor inputs from the local surrogate (step 205). These sensor inputs are used to create a contact message (step 210). The contact message is then transmitted to the remote computer (step 215). The remote mechanical surrogate is then commanded to mimic the actions experienced by the local surrogate (step 220). The loop continues until a contact encounter is completed (step 225). This is accomplished by allowing a user to terminate the activity.

As already described, the method provides for a full duplex physical contact experience. Mechanical surrogates 50 and 55 both comprise sensors and actuators. Hence, as the remote surrogate 55 is activated to mimic the physical contact the local surrogate 50 experiences, the remote surrogate 55 also provides sensory feedback. The feedback signal from each surrogate is subject to a process in which any induced action is attenuated. This prevents an oscillatory reaction between the two mechanical surrogates. This oscillatory reaction is much akin to the infinite reflections found between two parallel mirrors disposed in an opposing fashion.

There is an interface manager in the computer program that uses contact messages to communicate with a corresponding program executing on a remote computer. The contact messages that are exchanged between two computer programs comprise source and destination addresses so that the message can be routed from one computer to another. The actual body of the contact message comprises characteristic fields. The characteristic fields convey temperature, pressure and displacement information as perceived by the corresponding sensors. The interface manager in the computer program also manages the transmission and reception of video, audio and textual data using computer readable media.

Figure 7:
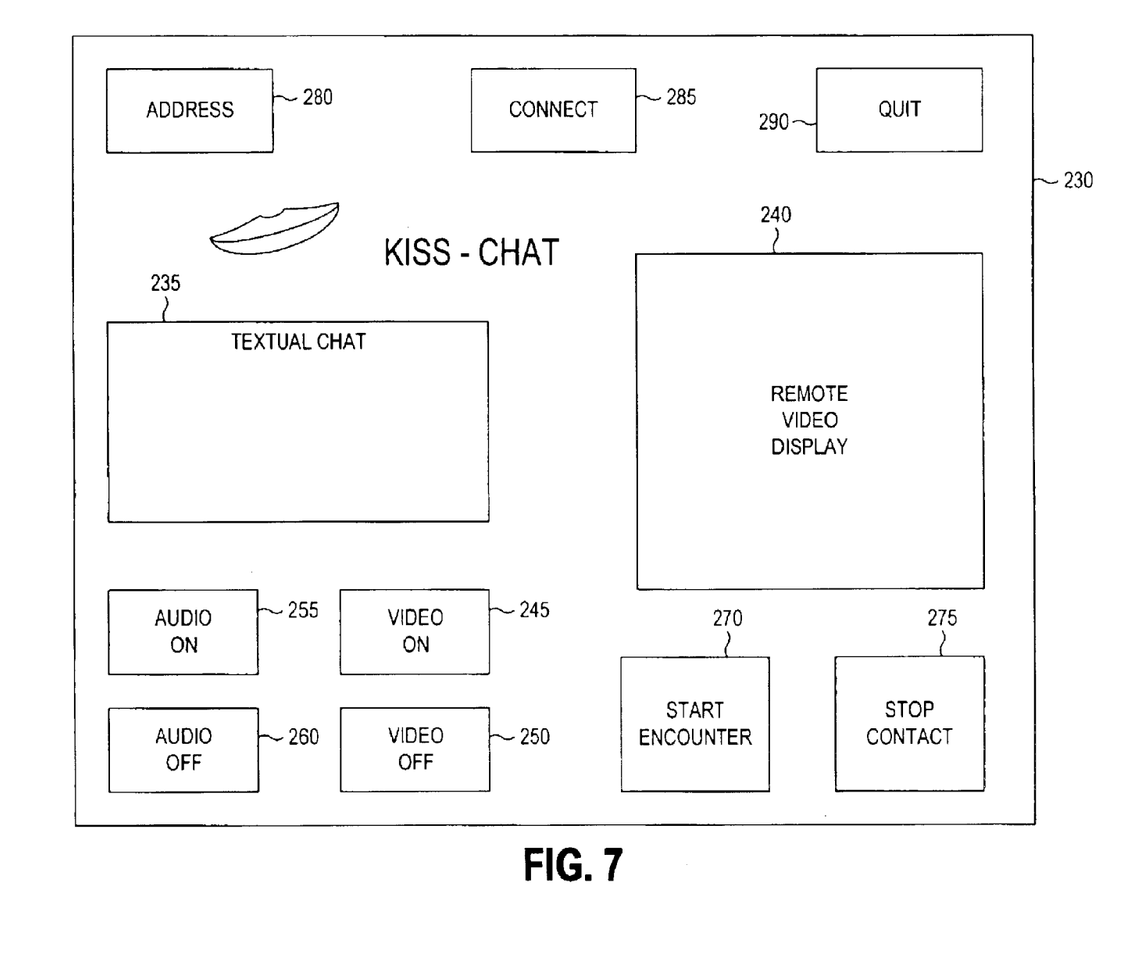
FIG. 7 is a pictorial representation of a graphical user interface used by a computer program that embodies the method of the present invention.

FIG. 7 is a pictorial representation of a graphical user interface used by a computer program that embodies the method of the present invention. The computer program uses a graphical user interface manager to present a graphical user interface (GUI) comprising a top-level window 230. Within the confines of the top-level window 230, the GUI comprises a textual chat window 235. Using the textual chat window 235, two users can communicate using keystrokes on their respective keyboards. In order to provide a level of privacy, the GUI allows the user to enable or disable audio or video transmission. This is done through the use of command buttons to turn audio on 255 or of 260 and other command buttons to turn video on 245 or off 250. The GUI further comprises a video presentation window 240 that is used to present video arriving from a remote instance of the program.

The GUI provides for identification of a target destination address with a dropdown selection dialog box 280. Once an address is selected, a connection can be established by selecting the connect command button 285. The connection can be terminated by selecting the quit command button 290. With a connection established, the computer program according to the present invention allows the user to start a physical contact encounter by selecting the start encounter command button 270. Terminating the encounter is easily accomplished by selecting the stop contact command button 275.

Alternative Embodiments

While this invention has been described in terms of several preferred embodiments, it is contemplated that alternatives, modifications, permutations, and equivalents thereof will become apparent to those skilled in the art upon a reading of the specification and study of the drawings. It is therefore intended that the true spirit and scope of the present invention include all such alternatives, modifications, permutations, and equivalents. Some, but by no means all of the possible alternatives are described herein.

What is claimed is:

1. A method for enabling remote physical contact comprising the steps of:

initiating a first mechanical surrogate attached to a first computing device wherein said first mechanical surrogate comprises a first model of an anatomical component comprising a first sensor to detect actions imparted on it, wherein said first sensor in said first mechanical surrogate comprises a thermal sensor;

accepting an address for a second computing device from a user;

establishing a communications link with said second computing device via said address;

initiating a second mechanical surrogate attached to said second computing device wherein said second mechanical surrogate comprises a second model of an anatomical component comprising a second actuator able to mimic actions imparted on said first mechanical surrogate, wherein said second actuator in said second mechanical surrogate is a heater-cooler;

receiving in said first computing device sensory input from said first mechanical surrogate that is indicative of an action imparted on said first mechanical surrogate;

creating in said first computing device a contact message reflecting said sensory input;

conveying said contact message to said second computing device using said communication link;

commanding said actuator in said second mechanical surrogate in accordance with said contact message in order to mimic said action imparted onto said first mechanical surrogate;

attenuating from sensory input from said second mechanical surrogate action components induced by said second actuator in said second mechanical surrogate resulting from said commanding;

receiving video information from a video camera attached to said first computing device;

compressing said video information;

conveying said video information to said second computing device using said communication link wherein said second computing device further comprises a graphics display;

displaying said video information on said graphics display of said second computing device;

receiving audio information from a microphone attached to said first computing device;

conveying said audio information to said second computing device using said communication link wherein said second computing device further comprises an audio output unit;

dispatching said audio information to said audio output unit of said second computing device;

receiving textual information from a keyboard attached to said first computing device;

conveying said textual information to said second computing device using said communication link wherein said second computing device further comprises a text display unit;

displaying said textual information on said text display unit of said second computing device; and, storing said contact message, said video information, said audio information and said text information for future playback.

2. The method of enabling remote physical contact according to claim 1 wherein said first mechanical surrogate is a counterpart to said second mechanical surrogate.

3. The method of enabling remote physical contact according to claim 1 wherein a second sensor in said first mechanical surrogate is either a displacement sensor, a pressure sensor or any combination thereof and wherein said actuator in said second mechanical surrogate is either a displacement actuator, a pressure actuator or any combination thereof.

4. The method of enabling remote physical contact according to claim 1 further comprising the steps of:
- receiving in said second computing device sensory input from said second mechanical surrogate wherein said second mechanical surrogate further comprises a second sensor that detects actions imparted on said second sensor and wherein said first mechanical surrogate further comprises a first actuator capable of mimicking actions imparted on said second mechanical surrogate;
- attenuating from said sensory input from said second mechanical surrogate action components induced by said second actuator in said second mechanical surrogate resulting from commands directed thereto according to said contact message to create a buffered sensory input;
- creating in said second computing device a contact message reflecting said buffered sensory input;
- conveying said contact message to said first computing device using said communication link; and
- commanding said first actuator in said first mechanical surrogate in accordance with said contact message in order to mimic said action imparted onto said second mechanical surrogate.

5. A computer program for affecting remote physical contact, said computer program executing in a tangible memory medium comprising:
- an interface manager that establishes connections with a remote computer program using a computer readable media;
- a sensor process that
  - receives sensor input signals from a first mechanical surrogate;
  - creates a first contact message that reflects the nature of the contact as indicated by said senor input signals;
  - conveys said first contact message to a remote process by way of said computer readable media;
- a response actuator process that
  - receives a second contact message from a remote process by way of the computer readable media;
  - commands an actuator in or on a second mechanical surrogate to cause said second mechanical surrogate to replicate a contact according to said second contact message wherein said second mechanical surrogate attenuates a sensory input from said second mechanical surrogate's action components induced by said actuator in said second mechanical surrogate resulting from said command; and,
- a video camera, a microphone and a keyboard attached to a first computing device, said first computing device capable of compressing and conveying video, audio and textual information to a second computing device using said computer readable media wherein said second computing device comprises a graphics display and speakers.

6. The computer program of claim 5 wherein said computer readable media is a computer network.

7. The computer program of claim 5 wherein said computer readable media is the Internet.

8. The computer program of claim 5 wherein said computer readable media is rotating media.

9. The computer program of claim 5 wherein said first contact message comprises a temperature characteristic field.

10. The computer program of claim 5 wherein said first contact message comprises a pressure characteristic field.

11. The computer program of claim 5 wherein said first contact message comprises a displacement characteristic field.

12. The computer program of claim 5 further comprising:
- a graphical user interface manager that presents a graphical user interface comprising an address acceptance window, a start encounter command button and a stop encounter command buttons and accepts an address from the address acceptance window and delivers the address to the interface manager for use as a destination address for contact messages.

13. The computer program of claim 12 wherein said graphical user interface manager further presents a textual chat window, accepts textual data from a keyboard and conveys that textual data to said interface manager for inclusion in said first contact message, and receives textual data from said interface manager and presents said textual data in said textual chat window.

14. The computer program of claim 12 wherein said graphical user interface manager further presents a video display window; and receives video data from the interface manager and presents the video data in the video display window.

* * * * *